United States Patent
Jabbarzadeh et al.

(10) Patent No.: US 11,698,344 B2
(45) Date of Patent: Jul. 11, 2023

(54) PH INDICATOR SWABS FOR BIOMONITORING AND DIAGNOSTICS

(71) Applicant: UNIVERSITY OF SOUTH CAROLINA, Columbia, SC (US)

(72) Inventors: Ehsan Jabbarzadeh, Columbia, SC (US); Sara Eslambolchimoghadam, Columbia, SC (US)

(73) Assignee: University of South Carolina, Columbia, SC (US)

( * ) Notice: Subject to any disclaimer, the term of this patent is extended or adjusted under 35 U.S.C. 154(b) by 926 days.

(21) Appl. No.: 16/545,459

(22) Filed: Aug. 20, 2019

(65) Prior Publication Data

US 2020/0072756 A1 Mar. 5, 2020

Related U.S. Application Data

(60) Provisional application No. 62/727,220, filed on Sep. 5, 2018.

(51) Int. Cl.
*G01N 21/80* (2006.01)
*A61B 5/145* (2006.01)

(52) U.S. Cl.
CPC ......... *G01N 21/80* (2013.01); *A61B 5/14539* (2013.01); *A61B 2562/12* (2013.01)

(58) Field of Classification Search
CPC . A61B 5/445; A61B 5/14539; A61B 2562/12; A61B 10/0048; A61B 10/007; G01N 21/80
See application file for complete search history.

(56) References Cited

U.S. PATENT DOCUMENTS

| | | |
|---|---|---|
| 3,972,328 A | 8/1976 | Chen |
| 4,192,785 A | 3/1980 | Chen et al. |
| 4,393,080 A | 7/1983 | Pawelchak et al. |
| 4,538,603 A | 9/1985 | Pawelchak et al. |
| 4,551,490 A | 11/1985 | Doyle et al. |
| 5,181,905 A | 1/1993 | Flam |
| 5,217,444 A | 6/1993 | Schoenfeld |
| 5,660,790 A | 8/1997 | Lawrence et al. |
| 5,823,953 A | 10/1998 | Roskin et al. |
| 5,897,834 A | 4/1999 | Lawrence et al. |

(Continued)

FOREIGN PATENT DOCUMENTS

| | | |
|---|---|---|
| CN | 105412981 | 3/2016 |
| CN | 106492260 | 3/2017 |

(Continued)

OTHER PUBLICATIONS

Armstrong, et al. "Diabetic foot ulcers and their recurrence" *New Eng. J. Med.* 376 (2017) pp. 2367-2375.

(Continued)

*Primary Examiner* — Sang H Nguyen
(74) *Attorney, Agent, or Firm* — Dority & Manning, P.A.

(57) ABSTRACT

Medical swabs incorporating a pH indicator in an absorbent crosslinked hydrogel matrix. The medical swabs can provide for visual monitoring of biological pH. The medical swabs can be used to monitor wounds, such as chronic wounds, burn wounds, surgical wounds, etc., as well as other biological fluids. The swabs can be used for early detection of chronic wounds and/or early detection of bacterial infections.

11 Claims, 4 Drawing Sheets

(56) References Cited

U.S. PATENT DOCUMENTS

| | | | |
|---|---|---|---|
| 5,910,447 | A | 6/1999 | Lawrence et al. |
| 6,106,461 | A | 8/2000 | Roskin et al. |
| 6,420,623 | B2 | 7/2002 | Augustine et al. |
| 6,570,050 | B2 | 5/2003 | Augustine et al. |
| 6,921,647 | B2* | 7/2005 | Kritzman ............ A61B 5/14539 |
| | | | 435/12 |
| 7,897,105 | B2 | 3/2011 | Chen |
| 9,724,078 | B2* | 8/2017 | Larsen ...................... A61P 7/04 |
| 9,855,364 | B2 | 1/2018 | Coomber |
| 2001/0051781 | A1 | 12/2001 | Augustine et al. |
| 2002/0029010 | A1 | 3/2002 | Augustine et al. |
| 2006/0228416 | A1* | 10/2006 | Faure ................. A61K 38/1709 |
| | | | 514/2.3 |
| 2007/0276207 | A1 | 11/2007 | Eagland et al. |
| 2008/0206293 | A1* | 8/2008 | Toreki ..................... A61P 31/04 |
| | | | 514/642 |
| 2008/0286148 | A1 | 11/2008 | Chen |
| 2009/0190135 | A1 | 7/2009 | Clarizia et al. |
| 2009/0275071 | A1 | 11/2009 | Brusilovsky et al. |
| 2013/0172781 | A1 | 7/2013 | Russo |
| 2015/0308994 | A1 | 10/2015 | Hammond et al. |
| 2016/0106880 | A1 | 4/2016 | Coomber |
| 2018/0093007 | A1 | 4/2018 | Coomber |
| 2018/0185844 | A1* | 7/2018 | Kerns ................ B01L 3/502715 |
| 2018/0353439 | A1 | 12/2018 | Jabbarzadeh et al. |
| 2018/0353440 | A1 | 12/2018 | Jabbarzadeh et al. |
| 2018/0353457 | A1 | 12/2018 | Jabbarzadeh et al. |
| 2018/0369165 | A1 | 12/2018 | Jabbarzadeh et al. |
| 2019/0070205 | A1 | 3/2019 | Jabbarzadeh et al. |
| 2020/0069478 | A1 | 3/2020 | Jabbarzadeh et al. |

FOREIGN PATENT DOCUMENTS

| | | |
|---|---|---|
| DE | 10016383 | 6/2001 |
| DE | 102011082716 | 3/2013 |
| GB | 2353357 | 2/2001 |
| JP | 2018048871 | 3/2018 |
| JP | 2018048872 | 3/2018 |
| KR | 20150033237 | 4/2015 |
| KR | 20160060519 | 5/2016 |
| WO | WO 2012/046087 | 4/2012 |
| WO | WO 2018/211458 | 11/2018 |

OTHER PUBLICATIONS

Bennison, et al. "The pH of wounds during healing and infection: A descriptive literature review" *Wound Pract. Res.: Au. J. Wound Man.* 25 (2017) pp. 63-69. (Abstract only).

Bowler, et al. "Wound microbiology and associated approaches to wound management" *Clin. Microbiol. Rev.* 14 (2001) pp. 244-269.

Choi, et al. "Intelligent pH indicator film composed of agar/potato starch and anthocyanin extracts from purple sweet potato" *Food Chem.* 218 (2017) pp. 122-128.

Credence Research. "Global Wound Debridement Products Market to Reach Worth US$ 493.1 Mn by 2025" (2018) pp. 1-2.

Dabiri, et al. "Choosing a wound dressing based on common wound characteristics" *Adv. Wound Care* 5 (2016) pp. 32-41.

Driver, et al. "The costs of diabetic foot: The economic case for the limb salvage team" *J. Vasc. Surg.* 52 (2010) pp. 17S-22S.

Gethin, G. "The significance of surface pH in chronic wounds" *Wounds UK* 3 (2007) pp. 52-56.

Golasz, et al. "Film with anthocyanins as an indicator of chilled pork deterioration" *Food Sci. Techn.* 33 (2013) pp. 155-162.

Han, et al. "Chronic wound healing: A review of current management and treatments" *Adv. Ther.* 34 (2017) pp. 599-610.

James, et al. "Biofilms in chronic wounds" *Wound Repair Regen.* 16 (2008) pp. 37-44.

Jones, et al. "The effect of pH on the extracellular matrix and biofilms" *Adv. Wound Care* 4 (2015) pp. 431-439.

Kuhn, et al. "Balancing the pressure ulcer cost and quality equation" *Nurs. Eco.* 10 (1992) pp. 353-359. (Abstract only).

Le, et al. "Recent developments in fibres and materials for wound management" *In. J. Fibre Text. Res.* 22 1997 pp. 337-347.

Liakos, et al. "Controlled antiseptic release by alginate polymer films and beads" *Carbohy. Polym.* 92 (2013) pp. 176-183.

Liang, et al. "A pH-Sensing Film from Tamarind Seed Polysaccharide with Litmus Lichen Extract as an Indicator" *Polymers* 10:13 (2017) pp. 1-10.

Liu, et al. "A pH-Indicating Colorimetric Tough Hydrogel Patch towards Applications in a Substrate for Smart Wound Dressings" *Polymers* 9:558 (2017) pp. 1-15.

Liu, L. "pH-Indicating Colorimetric Hydrogel for Wound Dressing and Medical Grade Silicone Adhesive for Skin Electronics: Towards Multifunctional Bionic Skin Patch" *U. Alberta* (2016) pp. 1-103.

MarketsandMarkets. "Wound Care Market worth $22.81 billion by 2022" *Markets and Markets* MD2611 (2017) pp. 1-2. https://www.marketsandmarkets.com/PressReleases/wound-care.asp.

McCallon, et al. "Optimizing wound bed preparation with collagenase enzymatic debridement" *J. Am. Coll. Clin. Wound Spec.* 6 (2014) pp. 14-23.

Mirani, et al. "An Advanced Multifunctional Hydrogel-Based Dressing for Wound Monitoring and Drug Delivery" *Adv. Healthcare Mater.* 6:1700718 (2017) pp. 1-26.

Ono, et al. "Increased wound pH as an indicator of local wound infection in second degree burns" *Burns* 41 (2015) pp. 820-824.

Schneider, et al. "Influence of pH on wound-healing: a new perspective for wound-therapy?" *Arch. Dermatol. Res.* 298 (2007) pp. 413-420.

Sen, et al. "Human skin wounds: A major and snowballing threat to public health and the economy" *Wound Rep. Regen.* 17 (2009) pp. 763-771.

Singer, et al. "Cutaneous wound healing" *New Eng. J. Med.* 341 (1999) pp. 738-746.

Sinha, S. "Wound debridement: Doing and teaching" *Prim. Int.: Au. J. Wound Man.* 15 (2007) pp. 162-164. (Abstract only).

* cited by examiner

PH INDICATOR SWABS FOR BIOMONITORING AND DIAGNOSTICS

CROSS REFERENCE TO RELATED APPLICATION

This application claims filing benefit of U.S. Provisional Patent Application Ser. No. 62/727,220, having a filing date of Sep. 5, 2018, entitled "pH-Indicating Swabs for Wound Biomonitoring and Diagnostics," which is incorporated herein by reference for all purposes.

FEDERAL RESEARCH STATEMENT

This invention was made with Government support under Grant No. 1811949, awarded by the National Science Foundation, and under Grant No. R03 EB026813, awarded by the National Institutes of Health. The Government has certain rights in the invention.

BACKGROUND

The pH of biological fluids can provide a good determination of the status of an individual. For instance, the normal pH of intact skin ranges from about 4.8 to about 6.0. When a wound occurs, the skin acidic milieu and pH is disrupted, exposing the more neutral pH of the underlying tissue (generally about pH 7.4). Over the course of successful healing and re-epithelialization the initial, more neutral, pH of the wound will drop due to various factors, including hypoxia and increased production of lactic acid. An acidic pH environment is considered to be beneficial during healing by increasing fibroblast proliferation and migration, promoting epithelization, regulating bacterial colonization, and facilitating the release of oxygen. Over the course of typical healing, an acute wound will pass through the physiological stages of inflammation, tissue formation, and remodeling in a timely fashion if the wound is kept clean; the skin will return to the healthy, slightly acidic range. If, however, wound healing is delayed, the pH will oscillate and become increasingly alkaline over time. At this stage, a wound can be considered to be a chronic wound. Chronic wound environments have been reported in the range of pH 7.15 to 8.93.

Chronic wounds, such as leg ulcers, foot ulcers, and pressure sores or decubitus ulcers caused by sustained external skin pressure, do not heal normally and can be detained in or not progress at all through the normal wound healing stages. Chronic wounds require intensive levels of care, and even with intensive treatment, may take years to fully heal or may never heal at all, causing long-term pain, as well as emotional and financial distress to the sufferer. An alkaline wound environment can be indicative of a chronic wound, and wounds of any sort having an elevated alkaline pH have been shown to have lower rates of healing than wounds in which the pH is lower. Alkaline wounds are also more likely to become infected and many wounds, especially chronic leg ulcers, are often colonized by intestinal, oral and resident dermal microorganisms.

The pH of biological fluids, with wound exudate being only one example, can affect many factors of the local environment, including oxygen release, angiogenesis, protease activity, macrophage and fibroblast activity, and bacterial toxicity. High pH can be an indicator of an existing infection, as pH increase from normal baseline is more favorable for bioburden of pathogenic microorganisms. Moreover, some bacteria produce ammonia, which in itself is necrotizing, and which can impair oxygenation of the tissues by further raising the pH and creating a self-sustaining cycle.

It is known that the measurement of pH facilitates early detection of infection, which can enable early therapeutic intervention and improve outcomes. Researchers have thus developed pH indicator compositions and devices to monitor body fluids. For instance, U.S. Pat. Nos. 5,660,790; 5,910, 447; and 5,897,834, and U.S. Published Patent Application Nos. 2009/0275071 and 2015/0308994 disclose devices and methods for analyzing the pH of various bodily secretions. Commercial examples of pH sensitive products include SwabCheck™ (Sigma), which includes a cellulose swab designed to collect a sample that is then transferred to an incubation tube; Amnicator™, which includes disposable swabs impregnated with nitrazine yellow dye; and VS-SENSE PRO™, which is a qualitative, visually readable swab for the evaluation vaginal fluid.

Unfortunately, many existing colorimetric pH indicator systems require a reagent to extract the biological materials from the collection device and to develop a detectable color, and are often subject to dye leaching, all of which adds to cost, complication, and potential error. Conventional pH indicators are also difficult to utilize as they require regular calibration, include fragile electrodes that must remain wet, and lack flexibility often necessary to access tissue or fluids of interest.

In clinical practice, diagnosis of infection has been based on initial determination of secondary parameters such as odor, presence of local pain, heat, swelling, discharge, and redness. For instance, a wound may be assessed visually, length and depth measurements may be taken, and digital photography may be used to track the visual condition and size of a wound. Unfortunately, many of these clinical indicators have a low predictive value of infection and confirmation of the suspected infection is required before treatment can begin. Swabbing of fluid from the area of the suspected infection followed by microbiology testing is a standard option for confirmation of bacterial colonization and identification of the strains associated with infection. Unfortunately, this process is time consuming and the time lag from onset of infection to detection is one of the biggest drawbacks associated with existing clinical diagnostics, as delay in diagnosis can delay treatment and negatively affect treatment outcome. Moreover, this process is labor-intensive and the multiple steps required in traditional swab-based diagnoses increase the potential for error, such as sampling errors, delays in transport of the swabs, errors in analytical procedures, and/or errors in reporting. While wound swabs have proven useful, the wait for testing results of the sample and the potential for introduction of error has limited their usefulness in the clinical setting, particularly for outpatients.

What is needed in the art is a convenient, rapid, and reliable method of detecting infection in early stages. There is an unmet need for diagnostic reagents and methods that enable early diagnosis of clinical infection, and which permit clinical diagnosis prior to manifestation of clinical symptoms of infection.

SUMMARY

According to one embodiment, disclosed is a medical swab that includes a surface and a crosslinked absorbent hydrogel matrix at the surface. The medical swab can also include a pH indicator retained within the crosslinked absorbent hydrogel matrix. The pH indicator exhibits a visually detectable color that is indicative of the pH of a fluid in contact with the pH indicator.

Also disclosed is a method for forming the medical swabs. For instance, a method can include forming a precursor solution comprising a pH indicator and a biocompatible polymer. The method can also include crosslinking the biocompatible polymer to form a crosslinked absorbent hydrogel matrix with the pH indicator retained within the matrix.

A method for detecting the pH of a biological fluid is also disclosed, which can include contacting a biological fluid or a tissue that carries or exudes the biological fluid with a medical swab, as described. Examination of the swab can visually determine the color of the pH indicator held in the swab, which can indicate the pH of the biological fluid. The method can be utilized in one particular embodiment for detecting the pH of a wound and can facilitate early diagnosis of infection in the wound, e.g., in a chronic wound.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
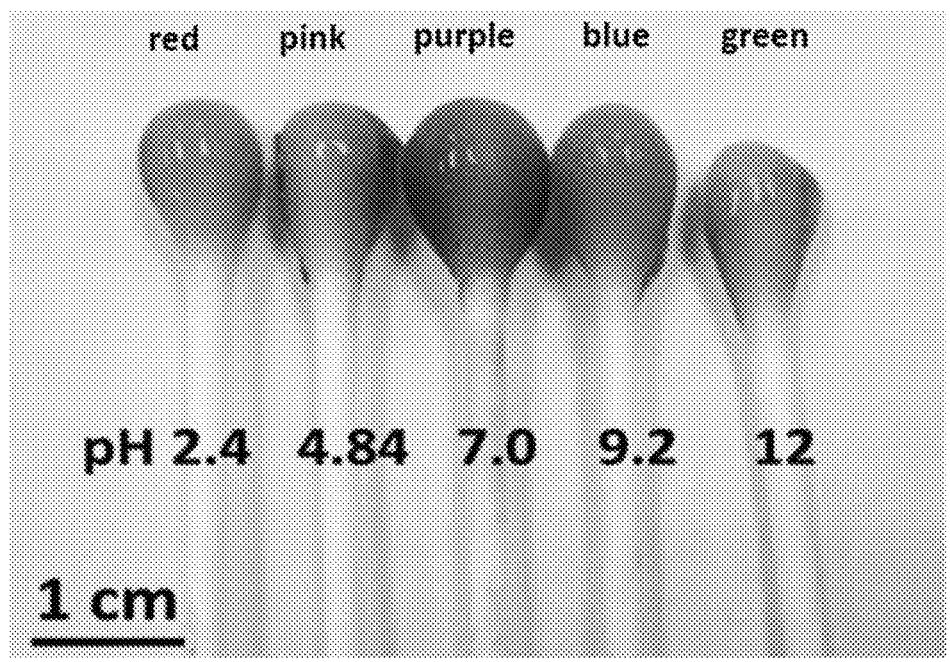
FIG. 1 illustrates colorimetric transition of the anthocyanin swabs in buffer solutions with different pH values. The original swab was purple at pH 7.0 (center) and it changed color from red to pink in acidic solutions (left) and blue to green (right) in basic solutions.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

The present disclosure is directed to medical swabs or swab-like structures that permit direct contact with an area of a patient's body, for instance an area such as a wound that is suspected of harboring a pathogenic micro-organism. The medical swabs incorporate a non-toxic composition that can provide for monitoring of biological pH in a simple, accurate, and rapid manner. Due to the ease of use and quick, visually detectable response of the medical swabs, pH monitoring can be carried out frequently and consistently, which can in one embodiment provide an on-going and accurate understanding of the dynamic condition of a biological fluid and the area from which the fluid is obtained.

The medical swabs include an absorptive crosslinked hydrogel and a pH indicator retained within the crosslinked hydrogel. The medical swabs can overcome disadvantages of previously known pH indicators by providing a non-toxic composition that enables simple and rapid monitoring of pH status of any area or biological fluid of interest, for instance in on-going monitoring of a wound for potential chronic wound development or monitoring an area for local or systemic bacterial infection. The swabs can be utilized in a one-step test, the results of which can be interpreted by merely looking at the swab, with no inspection or color detection equipment or analysis necessary.

The pH indicator of a medical swab can be any suitable colorimetric pH indicator that is capable of exhibiting a relatively rapid color change in the visible spectrum (light having a wavelength of from about 380 nm to about 740 nm) with change in pH. A pH indicator can in one embodiment detect pH between about pH 0 and about pH 14, though a pH indicator that detects pH within a smaller range is also encompassed. For instance, a pH indicator may be utilized that detects pH between about pH 5 and about pH 12, or about pH 6 and about pH 10 (e.g., a pH range expected in wound care). A suitable pH indicator can indicate changes in pH by way of a color change along the visual spectrum, with visually identifiable colors in the spectrum being associated with a particular pH. In addition, a pH indicator can exhibit a color change relatively rapidly, generally within a few minutes, e.g., about 5 minutes or less or about 1 minute or less in some embodiments.

Examples of suitable pH indicators can include, without limitation, litmus, anthocyanin, nitrazine yellow, brilliant yellow, cresol red, bromcresol purple, chlorophenol red, bromothymol blue, thymol blue, bromoxylenol blue, neutral red, phenol red, xylenol blue, m-cresol purple, orcein, erythrolitmin (or erythrolein), azolitmin, spaniolitmin, leucoorcein, and leucazolitmin, as well as combinations of indicators.

The medical swabs include the pH indicator retained within a crosslinked hydrogel matrix. Retention of the pH indicator within the hydrogel can prevent color change due to unintended contact with a fluid other than the biological fluid of interest and can also prevent leaching of the pH indicator from the medical swab.

The hydrogel matrix of the medical swab can be an absorptive and non-toxic material that can facilitate absorbing of a biological fluid of interest and movement of the fluid to the interior of the hydrogel, wherein it can contact the pH indicator retained therein. The hydrogel matrix can be formed from one or more non-toxic, biocompatible polymers that include, or can be modified to include, crosslinkable functionality. The matrix polymer can include synthetic and/or natural hydrogel-forming polymers. By way of example, and without limitation, hydrogel matrix polymers can include alginates, collagen or derivatives thereof, cellulose or derivatives thereof, poly(lactic-co-glycolic acid) (PLGA) or derivatives thereof, polycaprolactone (PCL) or derivatives thereof, as well as combinations of different polymers, e.g., blends or copolymers thereof.

According to one embodiment, the hydrogel matrix can include an alginate. Alginate is a naturally occurring anionic biocompatible polymer with low toxicity composed of a variety of alginic acids extracted from certain species of seaweeds. Alginate has been extensively investigated for many biomedical applications, including highly absorbent wound dressings. Alginate contains blocks of (1,4)-linked β-D-mannuronate (M) and α-L-guluronate (G) residues. Alginate has strong hydrophilicity, and as such, can form a highly absorbent wound dressing. Alginates are commercially available as pads, ropes, or ribbons from a variety of different suppliers. Alginate can be attractive for incorporation in a hydrogel matrix in one embodiment, as it is known as an approved material for epidermal applications and has excellent biocompatibility and mechanical properties. Additionally, calcium alginate is known as a natural hemostat that can be removed from a wound site limited or no trauma and discomfort.

The hydrogel matrix polymer is not limited to alginates, however, and other non-toxic, biocompatible hydrogel-forming polymers can be utilized in conjunction with or alternative to an alginate. For instance, in one embodiment, a hydrogel matrix can incorporate collagen, or a derivative thereof, for instance in the form of gelatin. Collagen is one of the main protein components of bone, cartilage, tendons, ligaments, and skin. Gelatin can be obtained from collagen by acidic or basic hydrolysis or thermal degradation of collagen, which leads to rupture of the collagen triple helix into the random coil structure of gelatin.

In one embodiment, the hydrogel matrix can include a cellulose polymer or a derivative of cellulose (e.g., cellulose acetate, sodium carboxymethyl cellulose, ethylcellulose, nitrocellulose, bacterial cellulose, etc.). Cellulose is the most abundant polysaccharide, and it is inexpensive with good processability, renewability, and ease of physical and chemical modification. It has good mechanical properties, good hydrolytic stability, low toxicity, and excellent biocompatibility.

PCL as may be incorporated in a wound dressing is a hydrophobic, semi-crystalline, resorbable, aliphatic polyester. The crystallinity decreases with increasing molecular weight, and PCL exhibits good solubility and low melting point (59° C.-64° C.), as well as excellent blend-compatibility, making it attractive for application in disclosed wound dressings. PCL can be biodegradable, but the degradation and resorption kinetics of PCL are relatively slow due to its hydrophobicity and high crystallinity, and as such, it can be beneficial in some embodiments as a component of disclosed hydrogels. PCL can be blended or co-polymerized with other polymers, such as PLA or PLGA, in order to modify its physical properties in a desirable fashion.

PLGA is a highly studied biodegradable polymer as may be incorporated in disclosed hydrogel. In vivo, it is hydrolyzed into the non-toxic lactic acid and glycolic acid monomers. PLGA is commercially available in different molecular weights and copolymer compositions. The rate of biodegradation of a PLGA polymer can be controlled through selection of the copolymer ratio and molecular weight.

To form the medical swab, an aqueous precursor solution can be formed that can include the pH indicator, the hydrogel matrix polymer and any other desired additives. For instance, a precursor solution can be formed including the pH indicator in an amount of from about 0.1% w/v to about 2% w/v. Depending upon the nature of the pH indicator, it may be preferred in some embodiments that the pH indicator is first dissolved by use of a suitable non-aqueous solvent (e.g., an alcohol such as ethanol or the like) and then combined with water to form an aqueous composition. Similarly, an aqueous solution including the pH indicator can include co-solvents, or the like, as are generally known in the art, to provide for dissolution of the pH indicator.

Following formation of an aqueous solution including the pH indicator, the hydrogel polymer can be added to the solution such that the precursor solution can include from about 0.5% w/v to about 20% w/v of the polymer. A precursor solution can also include any useful additives as are generally known in the art, which can be combined with the other components of a precursor solution in any desired order and in quantities as would be evident to one of skill in the art.

By way of example, in one embodiment a precursor solution can incorporate a plasticizer, which can improve the mechanical properties and flexibility of the medical swabs. Examples of suitable plasticizers can include, without limitation, dioctylphthalate; castor oil; diacetylated monoglycerides; diethyl phthalate; glycerin; mono- and di-acetylated monoglycerides; polyethylene glycol; propylene glycol; triacetin; triethyl citrate; bis-(2-butoxyethyl) adipate; and bis-(2-ethylhexyl) sebacate polyvinyl alcohol, polyvinyl alcohol, glycerol, and polyethylene glycol. When included, a precursor solution can generally include a plasticizer component in an amount of from 0 to about 20 w/v % of the precursor solution.

Other additives as may be included in a precursor solution can include materials as known in the art. For instance, a medical swab can incorporate one or more biologically active agents such as antimicrobial agents, antiseptic agents, antifungal agents, etc. in the precursor solution, which can then be retained in the crosslinked hydrogel matrix. Antimicrobial agents may include, for example, sources of oxygen and/or iodine (e.g., hydrogen peroxide or a source thereof and/or an iodide salt such as potassium iodide); antimicrobial metals, metal ions and salts, such as, for example, silver-containing antimicrobial agents (e.g., colloidal silver, silver oxide, silver nitrate, silver thiosulphate, silver sulphadiazine, or any combination thereof); or any combination thereof.

Other examples of additives of a precursor solution can include, without limitation, surfactants, colorants, chloride sources, and mixtures thereof. Additives to the precursor solution can encompass materials that are retained in the crosslinked hydrogel matrix of the medical swab, as well as materials that are not retained in the final product. For instance, an additive, e.g., a surfactant, may serve a purpose during formation of the medical swab and may be removed from the other components following its intended use and during a later stage of formation of the medical swab.

In some embodiments, a precursor solution can include a crosslinking agent and/or a crosslink initiator. In some embodiments, one or both of a crosslinking agent and a crosslink initiator can contact the precursor solution only at the time of crosslinking and following combination of the hydrogel polymer with the pH indicator to form the precursor solution. Conventional biocompatible cross-linking agents as are suitably used to provide the necessary mechanical stability and to control the properties of a hydrogel can be included in a precursor solution (or combined with a precursor solution at the time of crosslinking). When included in the precursor solution, the amount of crosslinking agent and/or crosslink initiator to be included will be readily apparent to those skilled in the art. For instance, a crosslinking agent can be included in an amount of from about 0.01% w/v to about 0.5% w/v, from about 0.05% w/v to about 0.4% w/v, or from about 0.08% to about 0.3% w/v, of the hydrogel precursor solution. Typical crosslinking agents can include, without limitation, tripropylene glycol diacrylate, ethylene glycol dimethacrylate, triacrylate, and methylene bis acrylamide. In one embodiment, a cationic crosslinking agent can be utilized. For example, a polyvalent elemental cation such as $Ca^{2+}$, $Mg^{2+}$, $Al^{3+}$, $La^{3+}$, or $Mn^{2+}$ can crosslink polymers of a hydrogel matrix.

When included, a precursor solution may include a crosslink initiator in standard amounts, e.g., up to about 5% w/v, for instance from about 0.002% w/v to about 2% w/v. In one embodiment, a precursor solution can include a photoinitiator, such as, and without limitation to, benzoyl radicals such as type I-α-hydroxy-ketones and benzilidimethyl-ketals (e.g., Irgacure 651, Irgacure 184, and Daracur 1173 as marketed by Ciba Chemicals), as well as combinations thereof.

A medical swab can include supporting substrates that can carry the crosslinked hydrogel matrix. For instance, a medical swab can include the crosslinked hydrogel matrix coated on an absorptive substrate that can facilitate absorption of a biological fluid of interest into the hydrogel matrix so as to encourage contact between the biological fluid and the pH indicator. An absorptive supporting substrate can be a fibrous substrate, e.g., a woven or non-woven absorptive textile, or an absorptive non-fibrous substrate, e.g., an open-pored absorptive foam. For instance, an absorptive supporting substrate can include a fibrous wadding, e.g., a cotton wool, or other cotton-based fibers, polyester fibers, polyurethane fibers, etc.; a medical gauze, or the like; or an absorbent foam, such as an open-celled hydrophilic polyurethane foam, a surgical sponge, or the like.

In such an embodiment, the precursor solution can generally be coated on the supporting substrate prior to crosslinking. For instance, a precursor solution can be coated on individual fibers of a fibrous supporting substrate and/or on the surface of a fibrous non-fibrous supporting substrate prior to crosslinking. Coating can be carried out by dip coating, spray coating, spin coating, or any other suitable coating methodology.

In one embodiment, a medical swab can include the crosslinked hydrogel matrix coated on a more stable, relatively non-pliable structural support, for instance a rod or other holding device formed of, e.g., a hollow or solid structure of a molded plastic (e.g., polyester), paper, or wood. The hydrogel matrix can be applied directly on such a structural support or, alternatively, can be coated on an absorptive supporting substrate, which in turn can be adhered to the structural support. For instance, a medical swab can be in the form of a typical cotton swab with one or both ends of a supporting rod carrying a cotton wool wadding. Individual fibers and/or the overall surface as a whole of an end cotton wool segment of the swab can be coated with the precursor solution prior to crosslinking.

It should be understood that the medical swab does not require an underlying support substrate, and in some embodiments, the crosslinked hydrogel matrix can exhibit suitable mechanical strength characteristics to serve as a medical swab, without the need for any supporting substrates or structural supports.

Following formation of the precursor solution and any post-formation processing (e.g., coating, forming, etc.), the precursor solution can be crosslinked to form the crosslinked hydrogel matrix and to secure the pH indicator within the crosslinked hydrogel matrix. In some embodiments, crosslinking can be initiated upon contact of a crosslinking agent with the precursor solution in conjunction with suitable crosslink initiation parameters as necessary (e.g., temperature or light). For instance, a hydrogel precursor solution containing sodium alginate as the hydrogel polymer can be combined with a divalent cation (via e.g., a $CaCl_2$ solution) and crosslinking can spontaneously occur via ion exchange. In other embodiments, crosslinking can be initiated by providing suitable crosslink parameters to initiate crosslinking of the precursor solution without the necessity of contact with an externally supplied crosslinking agent.

A medical swab can be utilized to sample a biological fluid of any source. For example, sample collection from the skin, mouth, nose, throat, sweat gland, urine, vagina or other locations, including both internal and external tissue locations, may be accomplished by bringing the crosslinked hydrogel matrix that is impregnated with the pH indicator dye into contact with the body fluid of interest, for instance by brushing or scraping a body surface with a swab. Upon contact, the absorptive hydrogel matrix can absorb fluid at the surface. As the fluid is absorbed into the hydrogel matrix, it will contact the retained pH indicator, and within a short time, the color of the indicator will change according to the pH value of the biological fluid, which in one embodiment can indicate the presence, type, or concentration of bacteria present in the fluid or in the area from which the fluid was obtained.

In one particular embodiment, the medical swabs can be utilized in monitoring the pH of wounds. Monitoring wound pH can help predict the progression of wound healing, as the pH of a wound can be indicative of the natural biochemical processes of healing, and alkalinization of a wound can play a part in chronic wound development. Furthermore, monitoring wound pH can provide early diagnosis of the presence of bacteria in the wound and imminent or existing infection. Wound pH can also impact the effectiveness of antibiotics or other treatments in a wound bed, and recognition of pH modulation in a wound, as well as active regulation of local pH, can be helpful in guiding management practices and in determining effective treatment strategies, which can improve patient outcomes.

Any type of wound can be monitored by use of the medical swabs, e.g., acute wounds, chronic wounds, burns of any degree, internal wounds, external wounds, etc. For instance, wounds including ulcers, burns, sunburns, traumatic injuries, bedsores, diabetic wounds, surgical wounds, and the like can be monitored. The medical swabs are not limited to wound treatment, however, and can be beneficially utilized in treatment of any form of skin disease or irregularity as well as for use in monitoring other biological fluids and tissue types. Non-limiting examples of biological fluids and tissues as may be monitored for pH abnormality by use of the medical swabs can include, without limitation, wounds and wound exudate, sweat or other skin exudate, vaginal surfaces and vaginal secretions, urine, saliva, amniotic fluids, blood, mucus, and nasal surfaces. Alterations in pH as may be detected by use of the medical swabs can provide for early diagnosis of serious medical conditions, in addition to pathogenic infections including ischemic syndromes such as coronary or peripheral arterial disease and angiogenesis-dependent disease.

Beneficially, the medical swabs can provide a qualitative, visually-readable result that is easily accessible to the clinicians, as well as non-clinical individuals, who wish to evaluate wound status. In some embodiments, the swabs can be used in conjunction with other, more traditional clinical examination. For instance, following determination of irregular pH in a fluid or tissue, further examination of the area can be carried out, such as more traditional diagnostic approaches known for determination of the number(s) and type(s) of pathogenic flora at the site using traditional laboratory and/or clinical diagnostic procedures. However, due to the objective measurement of pH state of a biological fluid available by assessing the color of the swab after contact of the swab with the area of interest, a treatment plan can be initiated prior to further examination by more traditional approaches, and the treatment plan can be based on the status of the wound as determined by the color of the swab applied to the surface. Earlier initiation of treatment can lead to improved outcomes for patients, as well as shorter treatment periods and decreased treatment costs.

The present disclosure may be better understood with reference to the Examples set forth below.

Example

Preparation of Litmus, Anthocyanins, and Bromothymol Blue

Anthocyanins solution was prepared by adding 55 g of chopped red cabbage to 90 mL of DI water, keeping at 90° C. for 1 hour, and filtering to obtain 90 mL of the final solution. About 0.1 g litmus dye (TCI, Tokyo, Japan) was added in 15 mL DI water and stirred to complete dilution. Bromothymol blue solution (Sigma Aldrich, USA) (0.1% w/v) was prepared by adding the dye to the water containing 0.2% v/v ethanol.

Preparation of Alginate Swabs Incorporated with pH Sensitive Dye

A solution of sodium alginate/glycerol (2% w/v-10% w/v) (Sigma-Aldrich-Fisher Scientific) was prepared in anthocyanin solution and homogenized at 800 rpm using stirrer for 1 hour. Homogenized solution was put into a sonication bath to remove the trapped air bubbles. Additionally, alginate/glycerol (2% w/v-10% w/v) containing 0.5% w/v litmus solution was prepared and homogenized for 1 hour. A solution of sodium alginate/bromothymol blue (2% w/v-0.1% w/v) was prepared by adding alginate to the dye solution following stirring for 1 hour.

Cotton swabs were coated through dipping in the alginate solution incorporated with a pH indicator dye solution for 1 hour followed by dipping in 2% w/v $CaCl_2$ for 10 minutes as crosslinker. pH indicator swabs were washed with DI water for 5 minutes to remove unreacted and excess $CaCl_2$ and dye.

Analysis of pH-Sensitive Swabs in Response to Different pH Environments

A glass microelectrode pH meter (VWR, USA) was used to measure the pH of the solutions of 0.1M potassium phosphate buffer, pH ranging from 2.4 to 12.0. The indicator swabs were exposed to the buffer solution, and afterwards, the color was photographed.

Colorimetric Detection of Bacterial Infections

A strain of Gram-negative *Pseudomonas aeruginosa* and Gram-positive *Staphylococcus aureus* and *E. coli* were cultured in Tryptic soy broth. These strains are highly prevalent in wounds and infections caused by these pathogens remain a common complication in acute and chronic wounds. Following 24-hour incubation, 200 μL bacteria in culture was deposited on the pH indicator swabs and photographed.

Cytotoxicity Assay (MTS)

In order to determine cell viability, normal human dermal fibroblasts (NHDFs) were cultured in growth media DMEM/10% FBS to reach 80% confluency. Cells were seeded at a density of $1\times10^5$ cell per 6 well plate in a total volume of 2 mL in each well. Cells were incubated at 37° C. and 5% $CO_2$ to allow for cell attachment and reach confluency. pH indicator swabs with 1 cm plastic support stick were sterilized through UV radiation for 2 hours and were soaked in 2 mL growth media for 2 hours. Eluates from the test swabs were added to the cells and exposed for 24 hours; untreated cells were used as control. Following 24-hour incubation, media containing 20% MTS solution was replaced with eluate media and incubated for 2 hours. Colored formazan absorbance which was produced by bio reduction of MTS tetrazolium compound in live cells was read at 490 nm using a Spectramax 190 spectrophotometer and cell viability was assessed.

Results

FIG. 1 demonstrates a gradient of colors for anthocyanin loaded swabs when exposed to buffer with different pH 2.4, 4.84, 7.0, 9.2, and 12.0. The original swab had pH of 7.0. Anthocyanin impregnated swabs turned red, pink, purple, blue, and green, respectively when exposed to the respective pH. Anthocyanins are a class of halochromatic substances which respond to the level of acidity in an environment with a color change. Anthocyanins pigments are responsible for the red, purple, and blue colors of many fruits and vegetables, including red and purple cabbage, beets, purple carrots, elderberry, hibiscus, purple potato, red and black currants, blueberries, cherries, purple grapes, and red and black raspberries. Anthocyanin pigment has a color gradient from orange to blue in the visible light spectrum, following the range of possible pH values.

Figure 2:
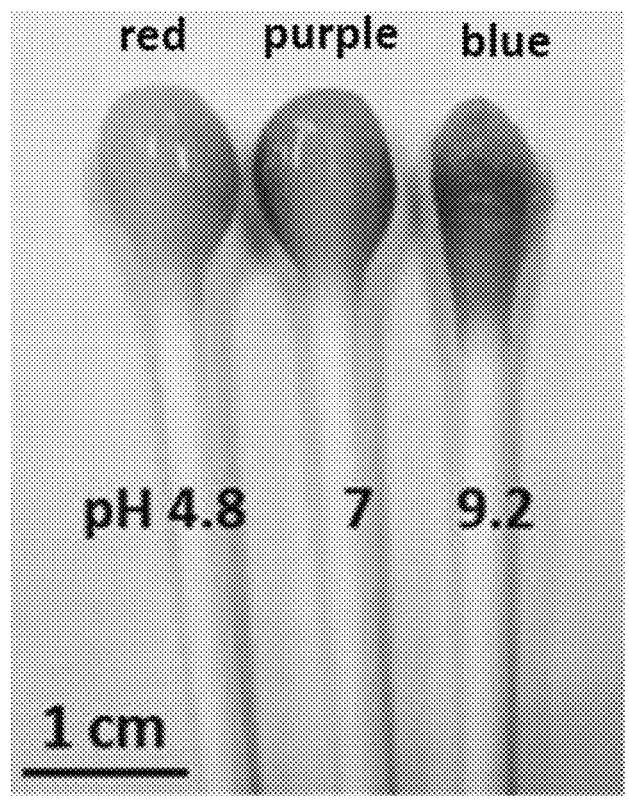
FIG. 2 illustrates colorimetric transition of litmus swabs in response to buffer pH 4.8 and 9.2. Original litmus swab was purple at neutral pH of 7.0 (center), when exposed to acidic buffer turned red (left) and in basic buffer turned blue (right).

FIG. 2 demonstrates litmus dye incorporated indicator swab exposed to different pH buffer solution. The litmus impregnated swab was originally red under acidic conditions, pH 4.2, turned blue under basic conditions, pH 9.2, and was purple in neutral pH 7.0.

Figure 3:
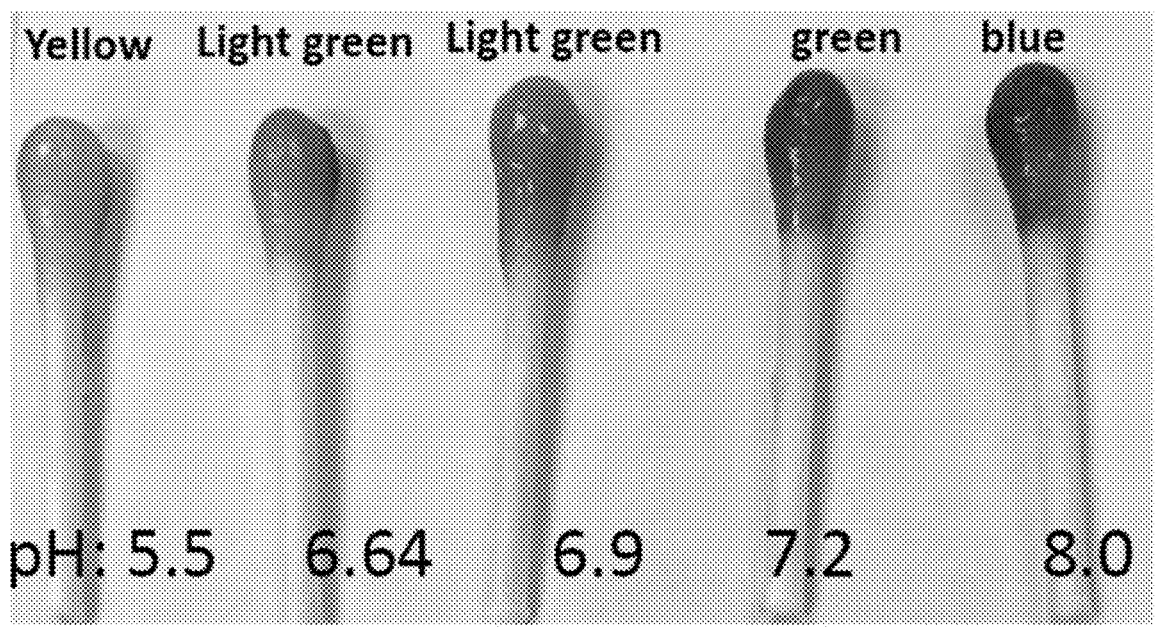
FIG. 3 illustrates colorimetric transition of bromothymol blue swabs in response to buffer with different pH. Original swab was yellow (left), when exposed to neutral buffer turned light green (center) and in basic buffer turned dark blue-green (right).

FIG. 3 demonstrates bromothymol blue loaded swab color change in response to pH changes. The swab was originally yellow, and swabs changed color to light green at pH of 7, and then shifted to blue-green at the higher pH of 8.

Figure 4:
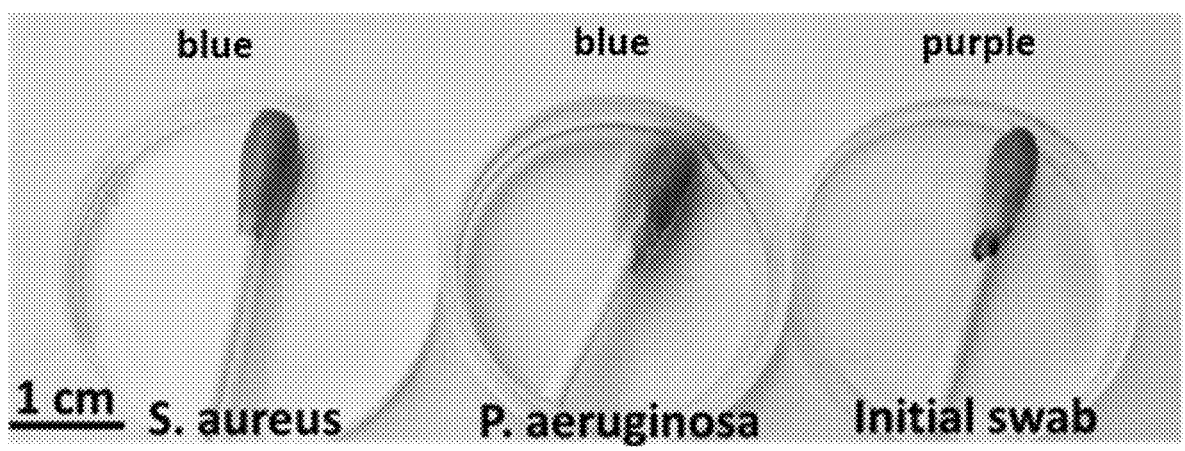
FIG. 4 illustrates colorimetric transition of the anthocyanin swabs in response to *Pseudomonas aeruginosa* and *Staphylococcus aureus*. Purple original swab (right) turned blue in the bacteria solutions.

FIG. 4 demonstrates color change of anthocyanin loaded swabs exposed to 200 μL of bacteria strains. The original purple color changed to blue in 10 minutes for both bacteria strains.

Figure 5:
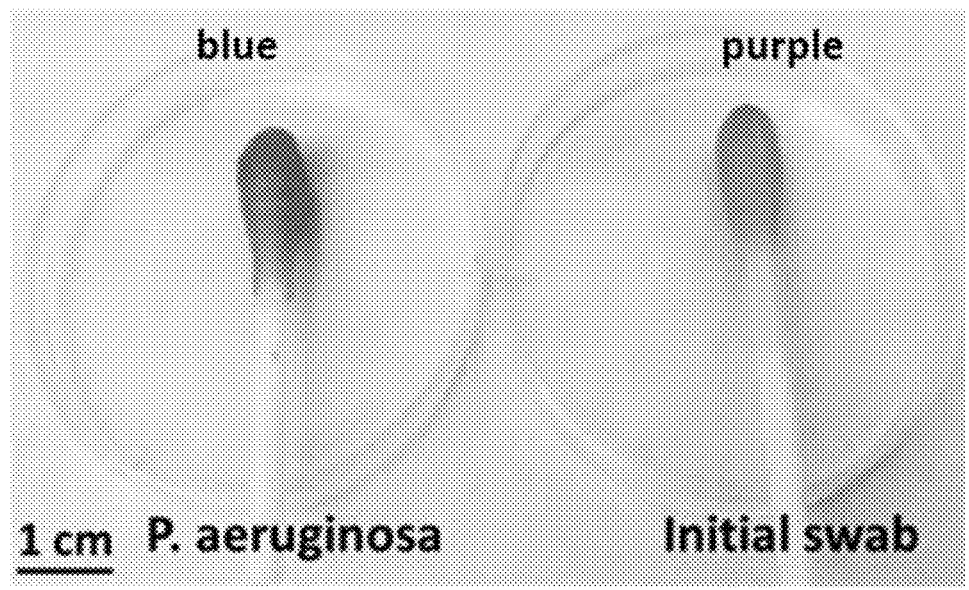
FIG. 5 illustrates colorimetric transition of the litmus swabs in response to *Pseudomonas aeruginosa*. Purple original swab (right) turned blue (left) in the bacteria solution.

FIG. 5 demonstrates litmus dye loaded swabs exposed to 200 μL of bacteria strains. The original purple swab turned blue in 10-minute exposure to bacteria in culture.

Figure 6:
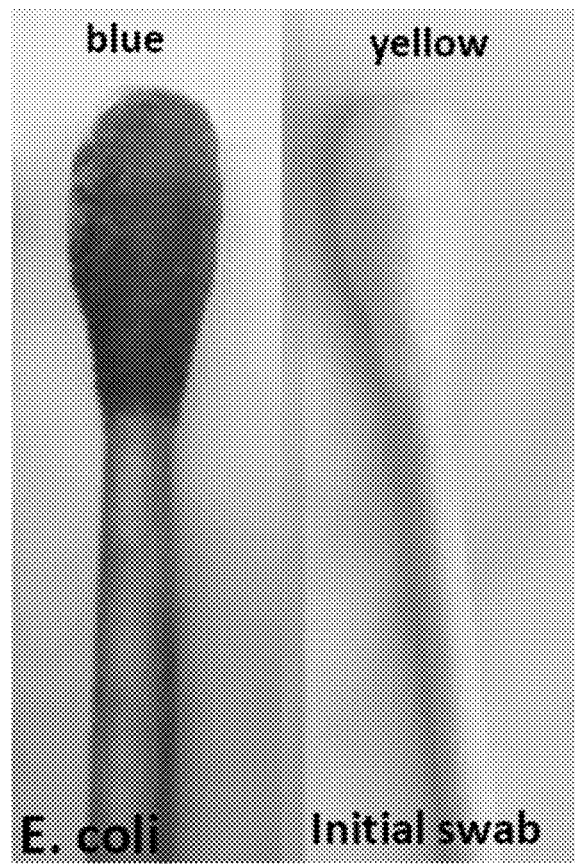
FIG. 6 illustrates colorimetric transition of the bromothymol blue swabs in response to *E. coli*. Yellow original swab (right) turned blue (left) in the bacteria solution.

FIG. 6 demonstrates bromothymol blue loaded swab exposed to 200 μL of *E. coli* bacteria strain. The color of the swab changed in 1 minute upon exposure to bacteria in culture.

Figure 7:
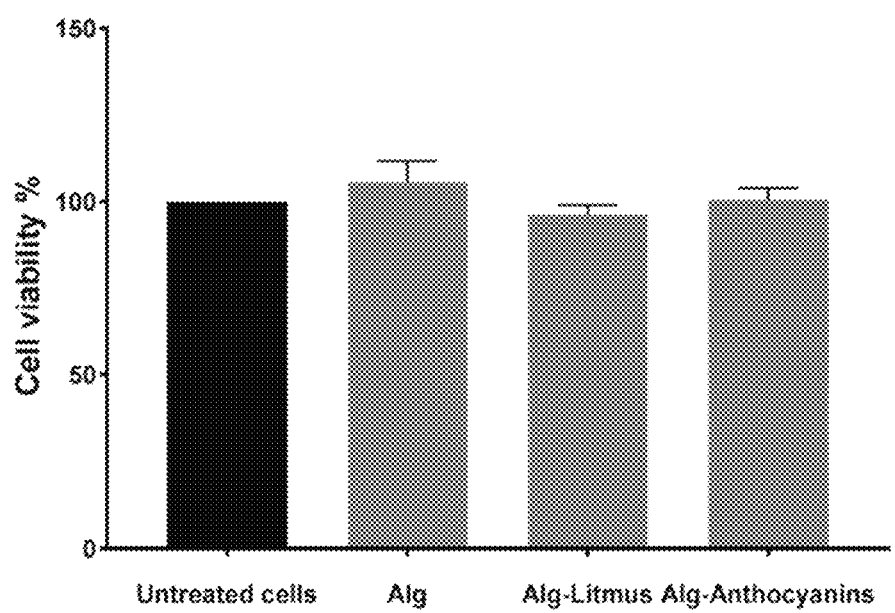
FIG. 7 illustrates the effect of swabs on cell viability of NHDFs. Cell viability (%) was calculated using an MTS assay after 24 h of exposure. No toxicity was observed.

FIG. 7 demonstrates cell viability results following 24-hour treatment with the swab extract. No cell toxicity was observed after 24 hours of exposure of swab extract to fibroblast cell line.

While certain embodiments of the disclosed subject matter have been described using specific terms, such description is for illustrative purposes only, and it is to be understood that changes and variations may be made without departing from the spirit or scope of the subject matter.

What is claimed is:

1. A medical swab comprising:
a swab surface;
a crosslinked absorbent hydrogel matrix comprising a biocompatible polymer at the swab surface;
a photoinitiator; and
a pH indicator retained within the crosslinked absorbent hydrogel matrix, the pH indicator exhibiting a detectable color change in the visible spectrum that is indicative of the pH of a fluid in contact with the pH indicator.

2. The medical swab of claim 1, the crosslinked absorbent hydrogel matrix comprising a plasticizer.

3. The medical swab of claim 2, the plasticizer comprising dioctylphthalate, castor oil, diacetylated monoglycerides, diethyl phthalate, glycerin, mono- and di-acetylated monoglycerides, polyethylene glycol, propylene glycol, triacetin, triethyl citrate, bis-(2-butoxyethyl) adipate, and bis-(2-ethylhexyl) sebacate polyvinyl alcohol, polyvinyl alcohol, glycerol, or polyethylene glycol.

4. The medical swab of claim 1, the biocompatible polymer comprising an alginate, a collagen, a gelatin, a cellulose, a poly(lactic-co-glycolic acid), a polycaprolactone, or derivatives or combinations thereof.

5. The medical swab of claim 1, the pH indicator comprising litmus, anthocyanin, nitrazine yellow, brilliant yellow, cresol red, bromcresol purple, chlorophenol red, bromothymol blue, thymol blue, bromoxylenol blue, neutral red, phenol red, xylenol blue, m-cresol purple, orcein, erythrolitmin (or erythrolein), azolitmin, spaniolitmin, leucoorcein, leucazolitmin, or any combination thereof.

6. The medical swab of claim 1, the medical swab further comprising a support substrate, wherein the crosslinked absorbent hydrogel matrix is coated on the support substrate.

7. The medical swab of claim 6, the support substrate comprising an absorptive substrate.

8. The medical swab of claim 7, the absorptive substrate comprising fibers, a foam, or a sponge.

9. The medical swab of claim 6, the support substrate comprising polyurethane, polyester, or cotton.

10. The medical swab of claim 6, the support substrate comprising a hollow or solid structure of molded plastic, paper or wood.

11. The medical swab of claim 1, wherein the photoinitiator comprises a benzoyl radical.

* * * * *